(12) United States Patent
Lubisch et al.

(10) Patent No.: US 7,026,311 B2
(45) Date of Patent: Apr. 11, 2006

(54) DIBENZODIAZEPINE DERIVATIVES, THEIR PREPARATION AND USE

(75) Inventors: Wilfried Lubisch, Heidelberg (DE); Roland Grandel, Dossenheim (DE); Wilfried Braje, Mannheim (DE); Thomas Subkowski, Ladenburg (DE); Reinhold Mueller, Schifferstadt (DE); Wolfgang Wernet, Neustadt (DE); Karla Drescher, Dossenheim (DE)

(73) Assignee: Abbott GmbH & Co., KG, Wiesbaden (DE)

( * ) Notice: Subject to any disclaimer, the term of this patent is extended or adjusted under 35 U.S.C. 154(b) by 393 days.

(21) Appl. No.: 10/041,556

(22) Filed: Jan. 10, 2002

(65) Prior Publication Data
US 2003/0139394 A1     Jul. 24, 2003

(51) Int. Cl.
A61K 31/55     (2006.01)
A61P 9/00      (2006.01)
C07D 487/06    (2006.01)

(52) U.S. Cl. .................. 514/219; 540/494; 540/555
(58) Field of Classification Search ............... 514/219; 540/494, 555
See application file for complete search history.

(56) References Cited

FOREIGN PATENT DOCUMENTS

WO   WO 01/16136 A2   3/2001
WO   WO 01/23390 A2   4/2001

OTHER PUBLICATIONS

Breslin et al., Synthesis and Anti-HIV-1 Activity of 4,5,6,7-Tetrahydro-5-methylimidazo[4,5,1-jk][1,4]benzodiazepin-2(1H)-one (TIBO) Derivatives, Journal of Medicinal Chemistry, vol. 38, No. 5, pp. 771-793, Mar. 1995.*
Burkle, Physiology and Pathophysiology of Poly(ADP-ribosyl)ation, BioEssays, vol. 23, No. 9, pp. 795-806, Sep. 2001.*
Burkart, et al., Mice lacking the poly (ADP-ribose) polymerase gene are resistant to pancreatic beta-cell destruction and diabetes development induced by streptozcin; Mar. 1999, pp. 314-319; vol. 5, No. 3, Nature Medicine.
Chen, et al., Potentiation of the antitumor activity of cisplatin in mice by 3-aminobenzamide and nicotinamide; (1998), pp. 303-307; vol. 22, Cancer Chemotherapy and Pharmacology.
Ehrlich, et al., Inhibition of the induction of collagenase by interleukin 1β in cultured rabbit synovial fibroblasts after treatment with the poly(ADP-ribose)-polymerase inhibitor 3-aminobensamide; Mar. 1995, pp. 171-172; vol. 15; Rheumatol Int.
Gäken, et al., Efficient Retroviral Infection of Mammalian Cells Is Blocked by Inhibition of Poly (ADP-Ribose) Polymerase Activity; Jun. 1996; pp. 3992-4000; vol. 70, No. 6; Journal of Virology.
Cuzzocrea, et al., Beneficial effects of 3-aminobenzamide, an inhibitor of poly (ADP-ribose) synthetase in a rat model of splanchnic artery occulosion and reperfusion; 1997; pp. 1065-1074; vol. 121; British Journal of Pharmacology.
Cuzzocrea, et al., Protective effects of 3-aminobenzamide, an inhibitor of poly (ADP-ribose) synthase in a carrageenan-induced model of local inflammation; 1998, pp. 67-76; vol. 342; European Journal of Pharmacology.
Ikai, et al., Immunohistochemical Demonstration of Poly (Adenosine Diphosphate-Ribose) Synthetase in Bovine Tissues; 1983; pp. 1261-1264; vol. 31, No. 11; The Hournal of Histochemistry and Cytochemistry.
Kröger, et al., Synergistic Effects of Thalidomide and Poly (ADP-Ribose) Polymerase Inhibition on Type II Collagen-Induced Arthritis in Mice; 1996; pp. 203-215;vol. 20, No. 2; Inflammation.
Shall, Sydney; ADP-Ribose in DNA Repair; A New Component of DNA Excision Repair; 1984; pp. 1-65; vol. II, Advances in Radiation Biology.
Kameoka, et al., Poly (ADP-ribose) Polymerase Is Involved in PMA-induced Activation of HIV-1 in U1 Cells by Modulating the LTR Function; 1999; pp. 285-289; vol. 262; Biochemical and Biophysical Research Communications.
Satoh, et al., Role of poly(ADP-ribose) formation of DNA repair; Mar. 1992; pp. 356-358; vol. 356; Nature.
Szabó, et al., Protection against peroxynitrite-induced fibroblast injury and arthritis development by inhibition of poly(ADP-ribose) synthase; Mar. 1998; 3867-3872; vol. 95; Proc. Natl. Acad. Sci. USA.
Weltin, et al., Immunosuppressive Activities of 6(5H)-Phenanthridinone, A New Poly (ADP-Ribose) Polymerase Inhibitor; 1995; pp. 265-271, vol. 17, No. 4; Int. J. Immunopharmac.
Thiemermann, et al., Inhibition of the activity of poly (ADP ribose) synthetase reduces ischemia -reperfusion injury in the heart and skeletal muscle; Jan. 1997; pp. 679-683; vol. 94; Proc. Natl. Acad. Sci. USA.

* cited by examiner

Primary Examiner—Brenda Coleman
(74) Attorney, Agent, or Firm—Wood, Phillips, Katz, Clark & Mortimer

(57) ABSTRACT

The invention relates to compounds of the formula I

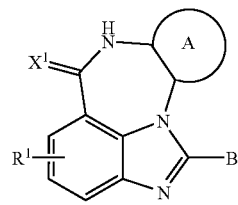

and their tautomeric forms, possible enantiomeric and diastereomeric forms and their prodrugs, and to their preparation and use, where A, B, $R^1$ and $X^1$ have the meanings given in the description.

11 Claims, No Drawings

DIBENZODIAZEPINE DERIVATIVES, THEIR PREPARATION AND USE

The present invention relates to novel dibenzodiazepine derivatives, to their preparation and to their use, as inhibitors of the enzyme poly(ADP-ribose) polymerase or PARP (EC 2.4.2.30), for preparing pharmaceuticals.

Poly(ADP-ribose) polymerase (PARP), or, as it is also termed, poly(ADP-ribose) synthase (PARS), is a regulatory enzyme which is found in cell nuclei (K. Ikai et al., J. Histochem. Cytochem. 1983, 31, 1261–1264). It is assumed that PARP plays a role in the repair of DNA breaks (M. S. Satoh et al., Nature 1992, 356, 356–358). Damage to, or breaks in, the DNA strands activate the PARP enzyme which, when it is activated, catalyses the transfer of ADP-ribose from NAD (S. Shaw, Adv. Radiat. Biol., 1984, 11, 1–69). At the same time, nicotinamide is released from the NAD. Other enzymes then reconvert nicotinamide into NAD, with this process consuming the energy source ATP. Accordingly, high activation of PARP would result in an unphysiologically high consumption of ATP, with this leading, in the extreme case, to cell damage and cell death.

It is known that free radicals, such as superoxide anion, NO and hydrogen peroxide can give rise to DNA damage in cells and thereby activate PARP. The formation of large quantities of free radicals is observed in a number of pathophysiological states and it is assumed that this accumulation of free radicals leads or contributes to the observed cell or organ damage. These pathophysiological states include, for example, ischemic states of organs, as in stroke and cardiac infarction (C. Thiemermann et al., Proc. Natl. Acad. Sci. USA, 1997, 94, 679–683), or ischemia of the kidneys, or else reperfusion damage as occurs, for example, following the lysis of cardiac infarction (see above: C. Thiemermann et al). Consequently, inhibition of the PARP enzyme could be a means of at least partially preventing or alleviating this damage. PARP inhibitors could consequently constitute a novel therapy principle for treating a number of diseases.

The PARP enzyme exerts an influence on the repair of DNA damage and could consequently also play a role in the therapy of cancer diseases, since a higher potential activity towards tumour tissue has been observed in combination with cytostatically active substances (G. Chen et al. Cancer Chemo. Parmacol. 1988, 22, 303).

Non-limiting examples of tumours are leukaemia, glioblastomers, lymphomas, melanomas and mammary and cervical carcinomas.

It has furthermore been found that PARP inhibitors are able to exhibit an immunosuppressive effect (D. Weltin et al., Int. J. Immunopharmacol. 1995, 17, 265–271).

It has also been discovered that PARP is involved in immunological disorders or diseases, such as rheumatoid arthritis and septic shock, in which the immune system plays an important role and that PARP inhibitors are able to exhibit a beneficial effect on the course of the disease (H. Kröger et al. Inflammation 1996, 20, 203–215; W. Ehrlich et al. Rheumatol. Int. 1995, 15, 171–172; C. Szabo et al., Proc. Natl. Acad. Sci. USA 1998, 95, 3867–3872; S. Cuzzocrea et al. Eur. J. Pharmacol. 1998, 342, 67–76).

Within the meaning of this invention, PARP is also understood as meaning isoenzymes of the above-described PARP enzyme.

Furthermore, the PARP inhibitor 3-aminobenzamide displayed protective effects in a model of circulatory shock (S. Cuzzocrea et al., Br. J. Pharmacol. 1997, 121, 1065–1074).

There are also experimental indications that inhibitors of the PARP enzyme could be of use as a means for treating diabetes mellitus (V. Burkart et al. Nature Med. 1999, 5, 314–319).

Experimental indications also show that PARP inhibitors could be of use as a means for treating viral infections, in particular infections with retroviruses (J. A. Gäken et al. J. Virol. 1996, 70, 3992–4000; M. Kameoka et al. Biochem Biophys Res Commun 1999, 262, 285–9).

Dibenzodiazepines and dibenzodiazepinones and their derivatives are a chemical class which has been frequently used in organic synthesis. However, derivatives of these compounds which additionally carry a fused-on imidazo ring, that is imidazodibenzodiazepinones, have not been described.

The compounds according to the invention, of the general formula I, have not hitherto been described and are consequently novel.

It has furthermore been found, surprisingly, that dibenzodiazepine derivatives which carry a fused-on ring are very effective inhibitors of the PARP enzyme.

The present invention describes novel dibenzodiazepine derivatives of the general formula I which are potent inhibitors of PARP.

The present invention relates to substituted dibenzodiazepine derivatives of the general formula I

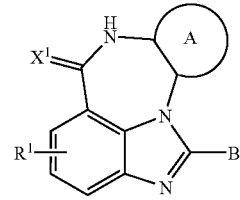

in which

A can be a saturated, unstaturated or partially unsaturated ring having at most 6 carbon atoms, an unsaturated or partially unsaturated ring having at most 5 carbon atoms and from 0 to 3 nitrogen atoms, from 0 to 2 oxygen atoms and/or from 0 to 2 sulphur atoms, and $X^1$ can be S, O and NH, and $R^1$ denotes hydrogen, chlorine, fluorine, bromine, iodine, branched and unbranched $C_1$–$C_6$-alkyl, OH, nitro, $CF_3$, CN, $NR^{11}R^{12}$, NH—CO—$R^{13}$, or O—$C_1$–$C_4$-alkyl, where $R^{11}$ and $R^{12}$, independently of each other, denote hydrogen or $C_1$–$C_4$-alkyl, and $R^{13}$ denotes hydrogen, $C_1$–$C_4$-alkyl, $C_1$–$C_4$-alkylphenyl or phenyl, and B can denote an unsaturated, saturated or partially unsaturated mono-, bi- or tri-cyclic ring having at most 15 carbon atoms or an unsaturated, saturated or partially unsaturated mono-, bi- or tri-cyclic ring having at most 14 carbon atoms and from 0 to 5 nitrogen atoms, from 0 to 2 oxygen atoms and/or from 0 to 2 sulphur atoms, which are in each case additionally substituted by one $R^4$ and at most 3 different or identical $R^5$ radicals, and one or two carbon, or sulphur, atoms can also carry one or two =O groups, such as keto groups, sulphones or sulphoxides, or denotes a radical $L_v$-Y-$M_w$, in which L can be a straight-chain or branched saturated or unsaturated carbon chain of from 1 to 8 C atoms, where each carbon atom can be substituted by one or two $R^4$ radicals and at most two different or identical $R^5$ radicals, and M possesses, independently of L, the same meaning as L, and Y denotes a bond or can be S, O or $NR^3$, where $R^3$ is hydrogen, branched or unbranched $C_1$–$C_6$-alkyl, $C_1$–$C_4$-alkylphenyl or phenyl, and v can denote 0 and 1, and w can be 0 and 1, and $R^4$ denotes hydrogen and -(D)$_p$-(E)$_s$-(F$^1$)$_q$-G$^1$-(F$^2$)$_r$-G$^2$-G$^3$, where D is S, $NR^{43}$ and O, E is phenyl,

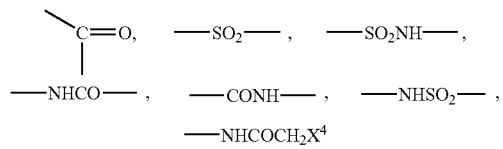

and $X^4$ can denote S, O or NH, and $F^1$ can be a straight-chain or branched, saturated or unsaturated carbon chain of from 1 to 8 C atoms and $F^2$ independently of $F^1$, possesses the same meaning as $F^1$, $G^1$ denotes a bond or can denote an unsaturated, saturated or partially unsaturated mono-, bi- or tri-cyclic ring having at most 15 carbon atoms or an unsaturated, saturated or partially unsaturated mono-, bi- or tri-cyclic ring having at most 14 carbon atoms and from 0 to 5 nitrogen atoms, from 0 to 2 oxygen atoms and/or from 0 to 2 sulphur atoms, which are in each case additionally substituted by at most 3 different or identical $R^5$ radicals, and one or two carbon, or sulphur, atoms can also carry one or two =O groups, and $G^2$ denotes $NR^{41}R^{42}$ and

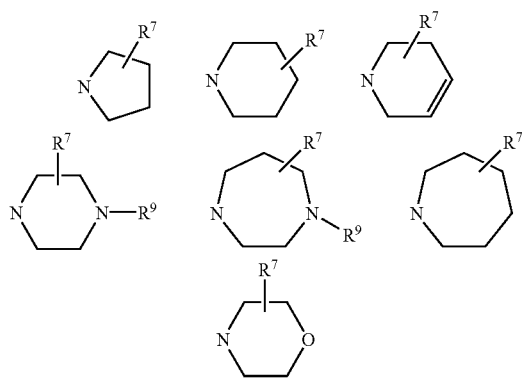

or a bond, and $G^3$ can denote an unsaturated, saturated or partially unsaturated mono-, bi- or tri-cyclic ring having at most 15 carbon atoms or an unsaturated, saturated or partially unsaturated mono-, bi- or tri-cyclic ring having at most 14 carbon atoms and from 0 to 5 nitrogen atoms, from 0 to 2 oxygen atoms and/or from 0 to 2 sulphur atoms, which are in each case additionally substituted by at most 3 different or identical $R^5$ radicals, and one or two carbon, or sulphur, atoms can also carry one or two =O groups, or denotes hydrogen, and p can denote 0 and 1, and s can be 0 and 1, and q can be 0 and 1, and r can be 0 and 1, and $R^{41}$ can be hydrogen, $C_1$–$C_6$-alkyl, where each carbon atom can additionally carry up to 2 $R^6$ radicals, phenyl, which can additionally carry at most 2 $R^6$ radicals, and (CH$_2$)$_t$—K, and $R^{42}$ can be hydrogen, $C_1$–$C_6$-alkyl, —CO—$R^8$, $CO_2$—$R^8$, $SO_2NH_2$, $SO_2$—$R^8$, —(C=NH)—$R^8$ and (C=NH)—$NHR^8$, and $R^{43}$ can be hydrogen and $C_1$–$C_4$-alkyl, and t can be 1, 2, 3 or 4, and K can be $NR^{11}R^{12}$, $NR^{11}$—$C_1$–$C_4$-alkylphenyl, pyrrolidine, piperidine, 1,2,5,6-tetrahydropyridine, morpholine, homopiperidine, piperazine, which can be additionally substituted by an alkyl radical $C_1$–$C_6$-alkyl, and homopiperazine, which can be additionally substituted by an alkyl radical $C_1$–$C_6$-alkyl, and $R^5$ can be hydrogen, chlorine, fluorine, bromine, iodine, OH, nitro, CF$_3$, CN, $NR^{11}R^{12}$, NH—CO—$R^{13}$, $C_1$–$C_4$-alkyl-CO—NH—$R^{13}$, COR$^8$, $C_0C_4$-alkyl-O—CO—$R^{13}$, $C_1$–$C_4$-alkylphenyl, phenyl, $CO_2$—$C_1$–$C_4$-alkyl and branched and unbranched $C_1$–$C_6$-alkyl, O—$C_1$–$C_4$-alkyl or S—$C_1$–$C_4$-alkyl where each C atom of the alkyl chains can carry up to two $R^6$ radicals and the alkyl chains can also be unsaturated, and $R^6$ can be hydrogen, chlorine, fluorine, bromine, iodine, branched or unbranched $C_1$–$C_6$-alkyl, OH, nitro, CF$_3$, CN, $NR^{11}R^{12}$, NH—CO—$R^{13}$ or O—$C_1$–$C_4$-alkyl, $R^7$ can be hydrogen, $C_1$–$C_6$-alkyl, phenyl, where the ring can be additionally substituted by up to two $R^{71}$ radicals, and an amine $NR^{11}R^{12}$ or a cyclic saturated amine having from 3 to 7 members which can additionally be substituted by an alkyl radical $C_1$–$C_6$-alkyl, and homopiperazine which can be additionally substituted by an alkyl radical $C_1$–$C_6$-alkyl, and where the radicals $R^{11}$, $R^{12}$ and $R^{13}$ in K, $R^5$, $R^6$ and $R^7$ can, independently of each other, assume the same meaning as $R^1$, and $R^{71}$ can be OH, $C_1$–$C_6$-alkyl, O—$C_1$–$C_4$-alkyl, chlorine, bromine, iodine, fluorine, CF$_3$, nitro or NH$_2$, and $R^8$ can be $C_1$–$C_6$-alkyl, CF$_3$, phenyl or $C_1$–$C_4$-alkylphenyl, where the ring can additionally be substituted by up to two $R^{81}$ radicals, and $R^{81}$ can be OH, $C_1$–$C_6$-alkyl, O—$C_1$–$C_4$-alkyl, chlorine, bromine, iodine, fluorine, CF$_3$, nitro or NH$_2$, and $R^9$ can be hydrogen, $C_1$–$C_6$-alkyl, $C_1$–$C_4$-alkylphenyl, $CO_2$—$C_1$–$C_4$-alkylphenyl, $CO_2$—$C_1$–$C_4$-alkyl, $SO_2$-phenyl, COR$^8$ and phenyl, where the phenyl rings can be additionally substituted by up to two $R^{91}$ radicals, and $R^{91}$ can be OH, $C_1$–$C_6$-alkyl, O—$C_1$–$C_4$-alkyl, chlorine, bromine, iodine, fluorine, CF$_3$, nitro or NH$_2$, and also their tautomeric forms and possible enantiomeric and diastereomeric forms and their prodrugs.

Preference is given to compounds of the formula I where

A represents a benzo ring, $X^1$ represents O, and $R^1$ is hydrogen.

Preference is given to compounds of the formula I, as indicated above, in which

B can denote an unsaturated, saturated or partially unsaturated mono-, bi- or tri-cyclic ring having at most 15 carbon atoms, an unsaturated, saturated or partially unsaturated mono-, bi- or tri-cyclic ring having at most 14 carbon atoms and from 0 to 5 nitrogen atoms, from 0 to 2 oxygen atoms and/or from 0 to 2 sulphur atoms, which are in each case additionally substituted by one $R^4$ and at most 3 different or identical $R^5$ radicals, and one or two carbon, or sulphur, atoms can also carry one or two =O groups.

The following radicals are particularly preferred for B:
B phenyl, cyclohexyl, piperidine, pyridine, pyrimidine, pyrrole, pyrazole, thiophene, furan, oxazole, naphthalene, piperazine, quinoline or pyrazine, which radicals can additionally be substituted by one $R^4$ or at most 2 $R^5$.

Particular preference is given to compounds of the formula I where
$R^4$ denotes $D_{0,1}$-$F^1_{0,1}$-$G^2$-$G^3$ where $G^3$ is hydrogen, and
D denotes O and $NR^{43}$, where $R^{43}$ is hydrogen and $C_1$–$C_3$-alkyl, and
$F^1$ denotes $C_2$–$C_4$-alkyl.

Preference is likewise given to compounds of formula I, where
$R^4$ denotes $G^1$-$F^1_{0,1}$-$G^2$-$G^3$ where $G^3$ is hydrogen, and
$F^1$ denotes $C_1$–$C_2$-alkyl.

Very particular preference is given to compounds of the formula I, where
$R^4$ denotes $G^1$-$F^1_{0,1}$-$G^2$-$G^3$ where $G^3$ is hydrogen, and
$G^1$ denotes imidazole or pyrrole which in each case can be additionally substituted by at most 3 different or identical $R^5$ radicals, and
$F^1$ denotes $C_1$–$C_2$-alkyl.

Preference is likewise given to compounds of the formula I as indicated above in which
B denotes a radical $L_v$-Y-$M_w$ in which
L can be a straight-chain or branched, saturated or unsaturated carbon chain of from 1 to 8 C atoms, where each carbon atom can be substituted by one or two $R^4$ radicals and at most two different or identical $R^5$ radicals, and
M independently of L, possesses the same meaning as L, and
Y denotes a bond or can be S, O or $NR^3$, where $R^3$ can be hydrogen, branched and unbranched $C_1$–$C_6$-alkyl, $C_1$–$C_4$-alkyl-phenyl or phenyl, and
v can denote 0 and 1, and
w can denote 0 and 1.

Of these, particular preference is given to compounds of the formula I where
L can be a carbon chain of from 1 to 8 C atoms, which chain contains at least one triple bond, where the carbon atoms of the chain can be substituted by one or two $R^4$ radicals and at most two different or identical $R^5$ radicals, and
v denotes 1, and
w can denote 0 and 1.

The compounds of the formula I can be used as racemates, as enantiomerically pure compounds or as diastereomers. If enantiomerically pure compounds are desired, they can be obtained, for example, by carrying out a classical racemate resolution of the compounds of the formula I, or their intermediates, using a suitable optically active base or acid.

Alkyl chains may in each case be branched or unbranched. Unbranched alkyl chains are preferred.

The invention also relates to compounds which are mesomers or tautomers of the compounds of the formula I.

The invention furthermore relates to physiologically tolerated salts of the compounds I which can be obtained by reacting compounds I with a suitable acid or base. Examples of suitable acids and bases are listed in Fortschritte der Arzneimittelforschung [Advances in drug research], 1966, Birkhäuser Verlag, Vol. 10, pp. 224–285. They include, for example, hydrochloric acid, citric acid, tartaric acid, lactic acid, phosphoric acid, methanesulphonic acid, acetic acid, formic acid, maleic acid, fumaric acid, etc., or sodium hydroxide, lithium hydroxide, potassium hydroxide, and Tris, respectively.

Prodrugs are understood as being those compounds which are metabolized into compounds of the general formula I in vivo. Typical prodrugs are phosphates, carbamates of amino acids, esters and others.

The preparation of the dibenzodiazepine derivatives I according to the invention has been outlined in Synthesis Scheme 1.

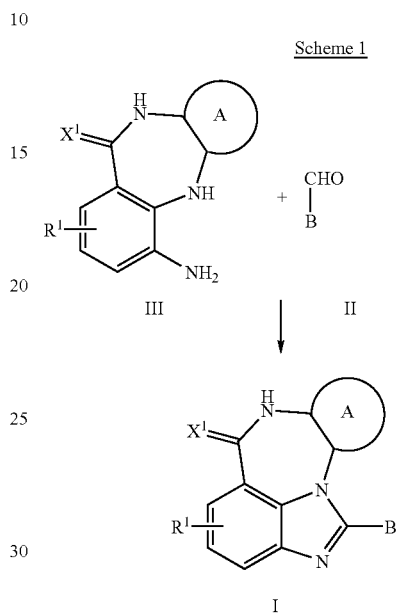

Scheme 1

Condensation of the aldehyde II with diamines III results in the dibenzodiazepine I, with the reaction preferably being carried out in polar solvents, such as ethanol or dimethylformamide, in the added presence of acids, such as acetic acid, at elevated temperature, as a rule 80–120° C. It is beneficial for the reaction if oxidizing agents, such as aqueous solutions of copper II salts, are added. The imine intermediate can also be oxidized using quinone derivatives.

The compounds III are synthesized, as shown in Scheme 2, by reacting a substituted nitrobenzoic ester IV, in which $R^2$ denotes branched or unbranched, saturated or unsaturated $C_1$–$C_6$-alkyl, with a suitable diamine in a polar solvent, such as for example dimethylformamide, in the presence of a base, such as potassium carbonate, at from 100° C. to 150° C., preferably at from 110° to 130° C., in particular at about 120° C., and subsequently hydrogenating in the presence of a suitable catalyst, such as 10% palladium on charcoal.

Scheme 2

$Y^1$ = Halogen

-continued

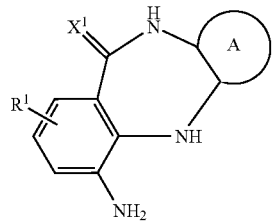

The substituted dibenzodiazepine derivatives I which are contained in the present invention are inhibitors of the enzyme poly(ADP-ribose)polymerase or PARP (EC 2.4.2.30).

The inhibitory effect of the substituted dibenzodiazepine derivatives I can be determined using an enzyme test which is already known in the literature, with a $K_i$ value being determined as the criterion of activity. In this way, the dibenzodiazepine derivatives I were assessed for their inhibitory effect on the enzyme poly(ADP-ribose)polymerase or PARP (EC 2.4.2.30).

The substituted dibenzodiazepine derivatives of the general formula I constitute inhibitors of poly(ADP-ribose) polymerase (PARP), or poly(ADP-ribose)synthase (PARS), as it is also termed, and can consequently be used for the treatment and prophylaxis of diseases which are associated with an increased activity of these enzymes.

The compounds of the formula I can be used for producing pharmaceuticals for treating damage following ischaemias, and for prophylaxis when ischaemias are expected in different organs.

The present dibenzodiazepine derivatives of the general formula I can accordingly be used for the treatment and prophylaxis of neurodegenerative diseases, and neuronal damage, particularly that which occurs following ischaemia, trauma, such as craniocerebral trauma, mass haemorrhages, subarachnoidal bleeding and stroke, and of neurodegenerative diseases, such as multiple infarction dementia, Alzheimer's disease and Huntington's disease, and of epilepsies, in particular of generalized epileptic seizures, such as petit mal and tonic-clonic seizures and partial epileptic seizures, such as temporal lobe, and complex-partial seizures, and, furthermore, for the treatment and prophylaxis of damage to the heart following cardiac ischaemias and damage to the kidneys following renal ischaemias, for example of acute renal insufficiency, of damage which is caused by medicinal therapies, such as in the case of cyclosporin treatment, of acute renal failure or of damage which occurs during and after a kidney transplantation. The compounds of the general formula I can furthermore be used for treating acute myocardial infarction and damage which occurs during and after its medicinal or mechanical lysis (for example using TPA, reteplase or streptokinase, or mechanically using a laser or rotablator) and microinfarctions, for example during and after heart valve replacement, aneurysms and heart transplantations. The present dibenzodiazepine derivatives I can also be used for treating a revascularization of critically stenosed coronary arteries, for example in association with PCTA and bypass operations, and critically stenosed peripheral arteries, for example leg arteries. Furthermore, the dibenzodiazepine derivatives I can be of use for treating tumours and their metastases, and be used for treating immunological diseases, such as inflammations and rheumatic diseases, such as rheumatoid arthritis, and also for treating diabetes mellitus, for treating sepsis and multiorgan failure, for example in association with septic shock, and for treating ARDS (acute respiratory distress syndrome). In addition, the dibenzodiazepine derivatives I can be employed for treating viral diseases, in particular infections with retroviruses, such as HIV.

The pharmaceutical preparations according to the invention comprise a therapeutically effective quantity of the compounds I in addition to the customary pharmaceutical auxiliaries.

For local external use, for example in powders, ointments or sprays, the active compounds can be present at the customary concentration. As a rule, the active compounds are present in a quantity of from 0.001 to 1% by weight, preferably of from 0.001 to 0.1% by weight.

For internal use, the preparations are administered in single doses. In a single dose, from 0.1 to 100 mg are administered per kg of bodyweight. The preparations may be administered daily, in one or more doses depending on the nature and severity of the diseases.

In addition to the active compound, the pharmaceutical preparations according to the invention comprise the customary carrier substances and diluents which are appropriate for the desired mode of administration. For local external use, it is possible to use auxiliary substances which are employed in the pharmaceutical industry, such as ethanol, isopropanol, ethoxylated castor oil, ethoxylated hydrogenated castor oil, polyacrylic acid, polyethylene glycol, polyethylene glycol stearate, ethoxylated fatty alcohols, paraffin oil, vaseline and lanolin. Lactose, propylene glycol, ethanol, starch, talc and polyvinylpyrrolidone are, for example, suitable for internal use.

Antioxidants such as tocopherol and butylated hydroxyanisole and butylated hydroxytoluene, taste-improving additives, stabilisers, emulsifiers and lubricants can also be present.

The substances which the preparation comprises in addition to the active compound, and also the substances which are used in producing the pharmaceutical preparations are toxicologically harmless and compatible with the given active compound. The pharmaceutical preparations are produced in a customary manner, for example by mixing the active compound with customary carrier substances and diluents.

The pharmaceutical preparations can be administered in a variety of modes of administration, for example perorally, parenterally, such as intravenously by means of infusion, subcutaneously, intraperitoneally and topically. Thus, possible preparation forms are tablets, emulsions, infusion and injection solutions, pastes, ointments, gels, creams, lotions, powders and sprays.

PHARMACOLOGICAL EXAMPLE

Inhibition of the enzyme poly(ADP-ribose)polymerase or PARP (EC 2.4.2.30)

A 96-well microtitre plate (Flacon) is coated with histones (Type II-AS; SIGMA H7755). For this, the histones are dissolved, to a concentration of 50 µg/ml, in carbonate buffer (0.05 M $NaHCO_3$; pH 9.4). The individual wells of the microtitre plates are incubated overnight with in each case 100 µl of this histone solution. After that, the histone solution is removed and the individual wells are incubated, at room temperature for 2 hours, with 200 µl of a 1% solution of BSA (bovine serum albumin) in carbonate buffer. The plates are then washed three times with washing buffer (0.05% Tween 10 in PBS). For the enzyme reaction, 50 µl of the enzyme reaction solution (5 µl of reaction buffer (1M Tris-HCl, pH 8.0, 100 mM MgCl$_2$, 10 mM DTT), 0.5 µl of PARP (c=0.22 µg/µl), 4 µl of activated DNA (SIGMA D-4522, 1 mg/ml in water), 40.5 µl of H$_2$O) are preincubated, per well, for 10 minutes with 10 µl of an inhibitor solution. The enzyme reaction is started by adding 40 µl of a substrate solution (4 µl of reaction buffer (see above), 8 µl of NAD solution (100 µM in H$_2$O), 28 µl of H$_2$O). The reaction time is twenty minutes at room temperature. The reaction is stopped by washing three times with washing buffer (see above). The plate is subsequently incubated for one hour, at room temperature, with a specific anti-poly-ADP-ribose antibody. The antibody employed was a monoclonal "10H" anti-poly(ADP-ribose)antibody (Kawamaitsu H et al. (1984) Monoclonal antibodies to poly(adenosine diphosphate ribose) recognize different structures. Biochemistry 23, 3771–3777). Polyclonal antibodies can also be used.

The antibodies were employed in a 1:5000 dilution in antibody buffer (1% BSA in PBS; 0.05% Tween 20). After the plate had been washed three times with washing buffer, there then followed a one-hour incubation, at room temperature, with the secondary antibody. In this case, a peroxidase-coupled anti-mouse IgG (Boehringer Mannheim) was used for the monoclonal antibody and a peroxidase-coupled anti-rabbit IgG (SIGMA A-6154) was used for the rabbit antibody, in each case in a 1:10,000 dilution in antibody buffer. After the plate had been washed three times with washing buffer, the colour reaction was then carried out, at room temperature for approx. 15 min, using 100 µl of colour reagent (SIGMA, TMB readymix, T8540)/well. The colour reaction is stopped by adding 100 µl of 2M H$_2$SO$_4$. After that, measurement takes place immediately (450 nm as against 620 nm; "Easy Reader" ELISA plate reader EAR340AT, SLT-Labinstruments, Austria). The IC50 value of an inhibitor which is being measured is the concentration of the inhibitor at which there is a half-maximum change in colour concentration.

EXAMPLES

Example 1

1-Phenylbenzo[b]imidazo[4,5,1-jk][1,4]benzodiazepin-6(7H)-one a) 4-Nitro-5,10-dihydro-11H-dibenzo [b,e][1,4]diazepin-11-one 18 g of methyl 2-chloro-3-nitrobenzoate, 35 g of 1,2-diaminobenzene and 23 g of potassium carbonate are heated to reflux for 4 hours in 400 ml of dimethylformamide. After the reaction has been completed, the reaction mixture is stirred into 2 l of water. The resulting precipitate is separated off by filtration, washed with water and dried in a vacuum-drying oven. 11.1 g of product are obtained.

b) 4-Amino-5,10-dihydro-11H-dibenzo[b, e ][1,4]diazepin-11-one dihydrochloride 11 g of the 1a product are initially introduced into 800 ml of dimethylformamide and hydrogenated in the presence of 1 g of 10% Pd on charcoal. After the reaction has come to an end, the catalyst is removed by filtration. The filtrate is concentrated in vacuo. 50 ml of 6M isopropanolic hydrochloric acid are added, at boiling heat, to a solution of the residue. The crop of crystals which is obtained following cooling is separated off by filtration and dried in a vacuum-drying oven. 10 g of product are obtained.

c) 1-Phenylbenzo[b]imidazo[4,5,1-jk][1,4]benzodiazepin-6(7H)-one

A solution of 1.5 g of the 1b product and 0.8 g of sodium acetate in 120 ml of methanol is stirred at room temperature for 30 min. Glacial acetic acid is added to the solution, after which a solution of 0.7 g of benzaldehyde in 25 ml of methanol is added dropwise. The reaction mixture is heated to reflux for 3 hours. After the mixture has been cooled down, a solution of 1.5 g of copper II acetate in 100 ml of water is added dropwise. The reaction mixture is heated to reflux for 2 hours. After the reaction has come to an end, the mixture is poured onto 100 ml of ammonia water. The product is extracted with ethyl acetate. After the solvent has been removed in vacuo, the crude product is purified by silica gel chromatography. 0.52 g of product is obtained.

$^1$H NMR (D$_6$-DMSO): δ=6.6 (1H), 6.9 (1H), 7.3–8.0 (9H), 10.3 (1H).

Example 2

1-[4-(4-Methylpiperazin-1-yl)phenyl]benzo[b]imidazo-[4,5,1-jk][1,4]benzodiazepin-6(7H)-one The product is obtained from 4-amino-5,10-dihydro-11H-dibenzo[b,e][1,4]diazepin-11-one dihydrochloride and 4-(4-methylpiperazin-1-yl)benzaldehyde in analogy with the directions in 1c.

$^1$H NMR (D$_6$-DMSO): δ=2.2 (3H), 2.45 (2H), 3.25 (2H), 6.7–8.9 (11H), 10.3 (1H).

Example 3

1-{4-[2-N,N-Diethylaminoeth-1-yloxy]phenyl}benzo-[b]imidazo[4,5,1-jk][1,4]benzodiazepin-6(7H)-one The product is obtained from 4-amino-5,10-dihydro-11H-dibenzo[b,e][1,4]diazepin-11-one dihydrochloride and 4-[2-N,N-diethylaminoeth-1-yloxy]benzaldehyde in analogy with the directions in 1c.

$^1$H NMR (D$_6$-DMSO) δ=0.95 (6H), 2.55 (4H), 2.8 (2H), 4.1 (2H), 6.7 (1H), 6.9 (1H), 7.0–8.0 (9H), 10.3 (1H).

Example 4

1-[4(1H-Imidazol-1-yl)phenyl]benzo[b]imidazo[4,5,1-jk][1,4]benzodiazepin-6(7H)-one The product is obtained from 4-amino-5,10-dihydro-11H-dibenzo[b,e][1,4]diazepin-11-one dihydrochloride and 4-(1H-imidazol-1-yl)benzaldehyde in analogy with the directions in 1c.

$^1$H NMR (D$_6$-DMSO) δ=6.7 (1H), 6.9 (1H), 7.15 (1H), 7.2 (1H), 7.4 (1H), 7.45 (1H), 7.8–8.0 (7H), 8.45 (1H), 10.3 (1H).

Example 5

1-(1-n-Propylpiperidin-4-yl)benzo[b]imidazo[4,5,1-jk][1,4]benzodiazepin-6(7H)-one The product is obtained from 4-amino-5,10-dihydro-11H-dibenzo[b,e][1,4]diazepin-11-one dihydrochloride and 1-n-propylpiperidine-4-carboxaldehyde in analogy with the directions in 1c.

¹H NMR (D₆-DMSO): δ=0.9 (3H), 1.7 (2H), 2.2–2.4 (4H), 2.9–3.2 (4H), 3.55 (2H), 3.7 (1H), 7.2–7.5 (5H), 7.9 (2H), 10.2 (1H), 10.8 (1H).

Example 6

1-Indol-3-ylbenzo[b]imidazo[4,5,1-jk][1,4]benzodiazepin-6(7H)-one

The product is obtained from 4-amino-5,10-dihydro-11H-dibenzo[b,e][1,4]diazepin-11-one dihydrochloride and indole-3-carboxaldehyde in analogy with the directions in 1c.

¹H NMR (D₆-DMSO): δ=6.85 (1H), 7.0 (1H), 7.1 (1H), 7.2 (2H), 7.4 (2H), 7.5 (1H), 7.8 (2H), 7.9 (2H), 10.25 (1H).

The following compounds according to the invention can be prepared in analogy with the above-described method:

1. 1-(4(4-n-Propylpiperazin-1-yl)phenyl)benzo[b]imidazo[4,5,1-jk][1,4]benzodiazepin-6(7H)-one
2. 1-(4(4-Isopropylpiperazin-1-yl)phenyl)benzo[b]imidazo[4,5,1-jk][1,4]benzodiazepin-6(7H)-one
3. 1-(4 (4-Benzylpiperazin-1-yl)phenyl)benzo[b]imidazo[4,5,1-jk][1,4]benzodiazepin-6(7H)-one
4. 1-(4(4-n-Butylpiperazin-1-yl)phenyl)benzo[b]imidazo[4,5,1-jk][1,4]benzodiazepin-6(7H)-one
5. 1-(4(4-Ethylpiperazin-1-yl)phenyl)benzo[b]imidazo[4,5,1-jk][1,4]benzodiazepin-6(7H)-one
6. 1-(4(2-N,N-Dimethylaminoeth-1-yloxy)phenyl)benzo[b]imidazo[4,5,1-jk][1,4]benzodiazepin-6(7H)-one
7. 1-(4-(2-Pyrrolidin-1-yleth-1-yloxy)phenyl)-benzo[b]imidazo[4,5,1-jk][1,4]benzodiazepin-6(7H)-one
8. 1-(4-(2-Piperazin-1-yleth-1-yloxy)phenyl)-benzo[b]imidazo[4,5,1-jk][1,4]benzodiazepin-6(7H)-one
9. 1-(4-(2-(4-Methylpiperazin-1-yl)eth-1-yloxy)phenyl)-benzo[b]imidazo[4,5,1-jk][1,4]benzodiazepin-6(7H)-one
10. 1-(4-(2-(4-Propylpiperazin-1-yl)eth-1-yloxy)phenyl)-benzo[b]imidazo[4,5,1-jk][1,4]benzodiazepin-6(7H)-one
11. 1-(4-(2-(4-Ethylpiperazin-1-yl)eth-1-yloxy)phenyl)-benzo[b]imidazo[4,5,1-jk][1,4]benzodiazepin-6(7H)-one
12. 1-(4-(2-(4-Benzylpiperazin-1-yl)eth-1-yloxy)phenyl)-benzo[b]imidazo[4,5,1-jk][1,4]benzodiazepin-6(7H)-one
13. 1-(4-(2-(4-Acetamidopiperazin-1-yl)eth-1-yloxy)phenyl)-benzo[b]imidazo[4,5,1-jk][1,4]benzodiazepin-6(7H)-one
14. 1-(4-(2-(4-Benzamidopiperazin-1-yl)eth-1-yloxy)phenyl)-benzo[b]imidazo[4,5,1-jk][1,4]benzodiazepin-6(7H)-one
15. 1-(4(4-Methylhomopiperazin-1-yl)phenyl)-benzo[b]imidazo[4,5,1-jk][1,4]benzodiazepin-6(7H)-one
16. 1-(4(4-Benzylhomopiperazin-1-yl)phenyl)-benzo[b]imidazo[4,5,1-jk][1,4]benzodiazepin-6(7H)-one
17. 1-(4(4-n-Butylhomopiperazin-1-yl)phenyl)-benzo[b]imidazo[4,5,1-jk][1,4]benzodiazepin-6(7H)-one
18. 1-(4(4-Ethylhomopiperazin-1-yl)phenyl)-benzo[b]imidazo[4,5,1-jk][1,4]benzodiazepin-6(7H)-one
19. 1-(4(Pyrrol-1-yl)phenyl)-benzo[b]imidazo[4,5,1-jk][1,4]benzodiazepin-6(7H)-one
20. 1-(4(3-Aminomethylpyrrol-1-yl)phenyl)-benzo[b]imidazo[4,5,1-jk][1,4]benzodiazepin-6(7H)-one
21. 1-(3(3-Aminomethylpyrrol-1-yl)phenyl)-benzo[b]imidazo[4,5,1-jk][1,4]benzodiazepin-6(7H)-one
22. 1-(4(3-Trifluoroacetamidomethylpyrrol-1-yl)phenyl)-benzo[b]imidazo[4,5,1-jk][1,4]benzodiazepin-6(7H)-one
23. 1-(4(2-Aminomethylpyrrol-1-yl)phenyl)-benzo[b]imidazo[4,5,1-jk][1,4]benzodiazepin-6(7H)-one
24. 1-(4(3-Formylpyrrol-1-yl)phenyl)-benzo[b]imidazo[4,5,1-jk][1,4]benzodiazepin-6(7H)-one
25. 1-(4-Methoxyphenyl)benzo[b]imidazo[4,5,1-jk][1,4]benzodiazepin-6(7H)-one
26. 1-(4-Chlorophenyl)benzo[b]imidazo[4,5,1-jk][1,4]benzodiazepin-6(7H)-one
27. 1-(4-Aminophenyl)benzo[b]imidazo[4,5,1-jk][1,4]benzodiazepin-6(7H)-one
28. 1-(4-Isopropylphenyl)benzo[b]imidazo[4,5,1-jk][1,4]benzodiazepin-6(7H)-one
29. 1-(3-Chlorophenyl)-5,6-dihydroimidazo[4,5,1-jk][1,4]benzodiazepin-7(4H)-one
30. 1-(3-Methylphenyl)benzo[b]imidazo[4,5,1-jk][1,4]benzodiazepin-6(7H)-one
31. 1-(3-Phenylphenyl)benzo[b]imidazo[4,5,1-jk][1,4]benzodiazepin-6(7H)-one
32. 1-(3-Isopropylphenyl)benzo[b]imidazo[4,5,1-jk][1,4]benzodiazepin-6(7H)-one
33. 1-(3-Fluorophenyl)benzo[b]imidazo[4,5,1-jk][1,4]benzodiazepin-6(7H)-one
34. 1-Piperidin-4-ylbenzo[b]imidazo[4,5,1-jk][1,4]benzodiazepin-6(7H)-one
35. 1-(1-Ethylpiperidin-4-yl)benzo[b]imidazo[4,5,1-jk][1,4]benzodiazepin-6(7H)-one
36. 1-(1-Isopropylpiperidin-4-yl)benzo[b]imidazo[4,5,1-jk][1,4]benzodiazepin-6(7H)-one
37. 1-Pyridin-4-ylbenzo[b]imidazo[4,5,1-jk][1,4]benzodiazepin-6(7H)-one
38. 1-Pyridin-3-ylbenzo[b]imidazo[4,5,1-jk][1,4]benzodiazepin-6(7H)-one
39. 1-Pyridin-2-ylbenzo[b]imidazo[4,5,1-jk][1,4]benzodiazepin-6(7H)-one
40. 1-[6-(1H-Imidazol-1-yl)pyridin-3-yl]benzo[b]imidazo[4,5,1-jk][1,4]benzodiazepin-6(7H)-one
41. 1-[6-(2-N,N-Dimethylamino-eth-1-ylmethylamino)pyridin-3-yl]benzo[b]imidazo[4,5,1-jk][1,4]benzodiazepin-6(7H)-one
42. 1-[6-(Pyrrol-1-yl)pyridin-3-yl]benzo[b]imidazo[4,5,1-jk][1,4]benzodiazepin-6(7H)-one
43. 1-[6-(3-Aminomethylpyrrol-1-yl)pyridin-3-yl]benzo[b]imidazo[4,5,1-jk][1,4]benzodiazepin-6(7H)-one
44. 1-[6-(4-Methylpiperazin-1-yl)pyridin-3-yl]benzo[b]imidazo[4,5,1-jk][1,4]benzodiazepin-6(7H)-one
45. 1-Thien-2-ylbenzo[b]imidazo[4,5,1-jk][1,4]benzodiazepin-6(7H)-one
46. 1-Indol-5-ylbenzo[b]imidazo[4,5,1-jk][1,4]benzodiazepin-6(7H)-one
47. 1-Indol-2-ylbenzo[b]imidazo[4,5,1-jk][1,4]benzodiazepin-6(7H)-one
48. 1-Quinolin-3-ylbenzo[b]imidazo[4,5,1-jk][1,4]benzodiazepin-6(7H)-one
49. 1-Isoquinolin-3-ylbenzo[b]imidazo[4,5,1-jk][1,4]benzodiazepin-6(7H)-one
50. 1-Quinoxalin-2-ylbenzo[b]imidazo[4,5,1-jk][1,4]benzodiazepin-6(7H)-one
51. 1-Naphth-2-ylbenzo[b]imidazo[4,5,1-jk][1,4]benzodiazepin-6(7H)-one
52. 1-(2-N,N-Dimethylaminoeth-1-ylamino)phenyl)benzo[b]imidazo[4,5,1-jk][1,4]benzodiazepin-6(7H)-one
53. 1-(2-N,N-Diethylaminoeth-1-ylamino)phenyl)benzo[b]imidazo[4,5,1-jk][1,4]benzodiazepin-6(7H)-one
54. 1-(2-Piperidin-1-yleth-1-ylamino)phenyl)benzo[b]imidazo[4,5,1-jk][1,4]benzodiazepin-6(7H)-one
55. 1-(2-Pyrrolidin-1-yleth-1-ylamino)phenyl)benzo[b]imidazo[4,5,1-jk][1,4]benzodiazepin-6(7H)-one
56. 1-(3-N,N-Dimethylaminoprop-1-ylamino)phenyl)benzo[b]imidazo[4,5,1-jk][1,4]benzodiazepin-6(7H)-one
57. 1-(3-N,N-Diethylaminoprop-1-ylamino)phenyl)benzo[b]imidazo[4,5,1-jk][1,4]benzodiazepin-6(7H)-one 58. 1-(3-Piperidin-1-ylprop-1-ylamino)phenyl)benzo[b]imidazo[4,5,1-jk][1,4]benzodiazepin-6(7H)-one
59. 1-(3-Pyrrolidin-1-ylprop-1-ylamino)phenyl)benzo[b]imidazo[4,5,1-jk][1,4]benzodiazepin-6(7H)-one
60. 1Cylcohexylbenzo[b]imidazo[4,5,1-jk][1,4]benzodiazepin-6(7H)-one
61. 1-(cis-4-Aminocyclohex-1-yl)benzo[b]imidazo[4,5,1-jk][1,4]benzodiazepin-6(7H)-one
62. 1-(4-Methoxycyclohex-1-yl)benzo[b]imidazo[4,5,1-jk][1,4]benzodiazepin-6(7H)-one
63. 1-(3-Aminophenyl)benzo[b]imidazo[4,5,1-jk][1,4]benzodiazepin-6(7H)-one
64. 1-(4-N,N-Diethylaminomethylphenyl)benzo-[b]imidazo[4,5,1-jk][1,4]benzodiazepin-6(7H)-one
65. 1-(4-(2-N,N-Diethylaminoeth-1-yl)phenyl)benzo[b]imidazo[4,5,1-jk][1,4]benzodiazepin-6(7H)-one
66. 1-(4-Hydroxyphenyl)benzo[b]imidazo[4,5,1-jk][1,4]benzodiazepin-6(7H)-one
67. 1-(4-Pyrrolidinemethylphenyl)benzo[b]imidazo-[4,5,1-jk][1,4]benzodiazepin-6(7H)-one
68. 1-(2-Methylthiophenyl)benzo[b]imidazo[4,5,1-jk][1,4]benzodiazepin-6(7H)-one
69. 1-(4Carboxyphenyl)benzo[b]imidazo[4,5,1-jk][1,4]benzodiazepin-6(7H)-one
70. 1-(3,5-bis(Trifluoromethyl)phenyl) benzo[b]imidazo[4,5,1-jk][1,4]benzodiazepin-6(7H)-one
71. 1-(4-tert-Butylphenyl)benzo[b]imidazo[4,5,1-jk][1,4]benzodiazepin-6(7H)-one
72. 1-(3-(Morpholin-4-ylmethyl)phenyl) benzo[b]imidazo[4,5,1-jk][1,4]benzodiazepin-6(7H)-one

The invention claimed is:
1. Compounds of the formula I

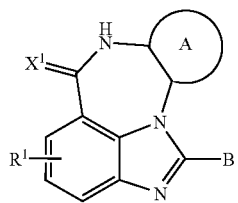

I in which
A denotes a saturated, unsaturated or partially unsaturated ring having at most 6 carbon atoms or an unsaturated or partially unsaturated ring having at most 5 carbon atoms and from 1 to 3 nitrogen atoms, one oxygen atom and/or one sulphur atom,
$X^1$ denotes S, O or NH,
$R^1$ denotes hydrogen, chlorine, fluorine, bromine, iodine, branched and unbranched $C_1$–$C_6$-alkyl, OH, nitro, $CF_3$, CN, $NR^{11}R^{12}$, NH—CO—$R^{13}$, or O—$C_1$–$C_4$-alkyl, where $R^{11}$ and $R^{12}$, independently of each other, denote hydrogen or $C_1$–$C_4$-alkyl, and $R^{13}$ denotes hydrogen, $C_1$–$C_4$-alkyl, $C_1$–$C_4$-alkylphenyl or phenyl,
B denotes an unsaturated, saturated or partially unsaturated mono-, bi- or tri-cyclic ring having at most 15 carbon atoms or an unsaturated, saturated or partially unsaturated mono-, bi- or tri-cyclic ring having at most 14 carbon atoms and from 0 to 5 nitrogen atoms, from 0 to 2 oxygen atoms and/or from 0 to 2 sulphur atoms, where the respective ring can be additionally substituted by one $R^4$ and at most 3 different or identical $R^5$ radicals, and one or two carbon, or sulphur, atoms can also carry one or two =O groups, or denotes a radical $L_v$-Y-$M_w$, in which
L denotes a straight-chain or branched saturated or unsaturated carbon chain of from 1 to 8 carbon atoms, where each carbon atom can be substituted by one or two $R^4$ radicals and at most two different or identical $R^5$ radicals,
M possesses, independently of L, the same meaning as L,
Y denotes a bond, S, O or $NR^{3'}$ where $R^3$ is hydrogen, branched or unbranched $C_1$–$C_6$-alkyl, $C_1$–$C_4$-alkylphenyl or phenyl, or when w is 0, Y is hydrogen,
v denotes 0 or 1, and
w denotes 0 or 1,
$R^4$ denotes hydrogen or -(D)$_p$-(E)$_s$-(F$^1$)$_q$-G$^1$-(F$^2$)$_r$-G$^2$-G$^{3'}$ where
D denotes S, $NR^{43}$ or O,
E denotes phenyl,

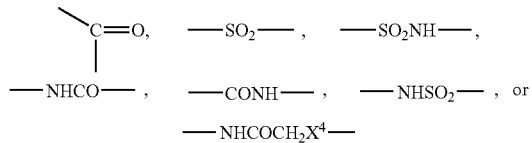

$X^4$ denotes S, O or NH,
$F^1$ denotes a straight-chain or branched, saturated or unsaturated carbon chain of from 1 to 8 carbon atoms,
$F^2$ independently of $F^1$, possesses the same meaning as $F^1$,
$G^1$ denotes a bond, an unsaturated, saturated or partially unsaturated mono-, bi- or tri-cyclic ring having at most 15 carbon atoms or an unsaturated, saturated or partially unsaturated mono-, bi- or tri-cyclic ring having at most 14 carbon atoms and from 0 to 5 nitrogen atoms, from 0 to 2 oxygen atoms and/or from 0 to 2 sulphur atoms, where the respective ring can be additionally substituted by at most 3 different or identical $R^5$ radicals, and one or two carbon and/or sulphur atoms can also carry one or two =O groups,
$G^2$ denotes $NR^{41}R^{42}$,

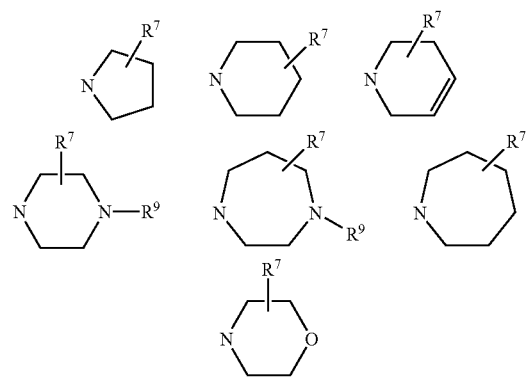

or a bond,
$G^3$ denotes an unsaturated, saturated or partially unsaturated mono-, bi- or tri-cyclic ring having at most 15 carbon atoms or an unsaturated, saturated or partially unsaturated mono-, bi- or tri-cyclic ring having at most 14 carbon atoms and from 0 to 5 nitrogen atoms, from 0 to 2 oxygen atoms and/or from 0 to 2 sulphur atoms where the respective ring is additionally substituted by at most 3 different or identical $R^5$ radicals, and one or two carbon or sulphur atoms can also carry one or two =O groups, or denotes hydrogen, p denotes 0 or 1,
s denotes 0 or 1,
q denotes 0 or 1,
r denotes 0 or 1, $R^{41}$ denotes hydrogen, $C_1$–$C_6$-alkyl, where each carbon atom can additionally carry up to 2 $R^6$ radicals, phenyl, which can additionally carry at most 2 $R^6$ radicals, or $(CH_2)_t$-K, $R^{42}$ denotes hydrogen, $C_1$–$C_6$-alkyl, —CO—$R^8$, $CO_2$—$R^8$, $SO_2NH_2$, $SO_2$—$R^8$, —(C=NH)—$R^8$ or (C=NH)—$NHR^8$, $R^{43}$ denotes hydrogen and $C_1$–$C_4$-alkyl, t denotes 1, 2, 3 or 4, K denotes $NR^{11}R^{12}$, $NR^{11}$—$C_1$–$C_4$-alkylphenyl, pyrrolidine, piperidine, 1,2,5,6-tetrahydropyridine, morpholine, homopiperidine, piperazine, which can be additionally substituted by an alkyl radical $C_1$–$C_6$-alkyl, and homopiperazine, which can be additionally substituted by an alkyl radical $C_1$–$C_6$-alkyl, $R^5$ denotes hydrogen, chlorine, fluorine, bromine, iodine, OH, nitro, $CF_3$, CN, $NR^{11}R^{12}$, NH—CO—$R^{13}$, $C_1$–$C_4$-alkyl-CO—NH—$R^{13}$, $COR^8$, $C_0$–$C_4$-alkyl-O—CO—$R^{13}$, $C_1$–$C_4$-alkyl-phenyl, phenyl, $CO_2$—$C_1$–$C_4$-alkyl and branched and unbranched $C_1$–$C_6$-alkyl, O—$C_1$–$C_4$-alkyl or S—$C_1$–$C_4$-alkyl where each C atom of the alkyl chains can carry up to two $R^6$ radicals and the alkyl chains can be unsaturated, $R^6$ denotes hydrogen, chlorine, fluorine, bromine, iodine, branched or unbranched $C_1$–$C_6$-alkyl, OH, nitro, $CF_3$, CN, $NR^{11}R^{12}$, NH—CO—$R^{13}$ or O—$C_1$–$C_4$-alkyl, $R^7$ denotes hydrogen, $C_1$–$C_6$-alkyl, phenyl, where the phenyl ring can be additionally substituted by up to two $R^{71}$ radicals, and an amine $NR^{11}R^{12}$ or a cyclic saturated amine having from 3 to 7 members which can additionally be substituted by an alkyl radical $C_1$–$C_6$-alkyl, and homopiperazine which can be additionally substituted by an alkyl radical $C_1$–$C_6$-alkyl, where the radicals $R^{11}$, $R^{12}$ and $R^{13}$, independently of each other, have the same meaning as $R^1$, $R^{71}$ denotes OH, $C_1$–$C_6$-alkyl, O—$C_1$–$C_4$-alkyl, chlorine, bromine, iodine, fluorine, $CF_3$, nitro or $NH_2$, $R^8$ denotes $C_1$–$C_6$-alkyl, $CF_3$, phenyl or $C_1$–$C_4$-alkylphenyl, where the ring can additionally be substituted by up to two $R^{81}$ radicals, $R^{81}$ denotes OH, $C_1$–$C_6$-alkyl, O—$C_1$–$C_4$-alkyl, chlorine, bromine, iodine, fluorine, $CF_3$, nitro or $NH_2$, $R^9$ denotes hydrogen, $C_1$–$C_6$-alkyl, $C_1$–$C_4$-alkylphenyl, $CO_2$—$C_1$–$C_4$-alkylphenyl, $CO_2$—$C_1$–$C_4$-alkyl, $SO_2$-phenyl, $COR^8$ or phenyl, where the phenyl rings can be additionally substituted by up to two $R^{91}$ radicals, $R^{91}$ denotes OH, $C_1$–$C_6$-alkyl, O—$C_1$–$C_4$-alkyl, chlorine, bromine, iodine, fluorine, $CF_3$, nitro or $NH_2$, and also their tautomeric forms and possible enantiomeric and diastereomeric forms.

2. Compounds of the formula I according to claim 1, in which
A denotes a benzo ring,
$X^1$ denotes O, and
$R^1$ denotes hydrogen.

3. Compounds of the formula I according to claim 1 in which
B denotes phenyl, cyclohexyl, piperidine, pyridine, pyrimidine, pyrrole, pyrazole, thiophene, furan, oxazole, naphthalene, piperazine, quinoline, pyrazine or indole, each of which can be substituted by one $R^4$ or at most 2 $R^5$.

4. Compounds of the formula I according to claim 1, in which
L denotes a carbon chain which has from 1 to 8 carbon atoms and which contains at least one triple bond, where the carbon atoms of the chain can be substituted by one or two $R^4$ radicals and at most two different or identical $R^5$ radicals,
v denotes 1, and
w denotes 0 or 1.

5. Compounds of the formula I according to claim 1, in which
$R^4$ denotes $D_{0,1}$-$F^1_{0,1}$-$G^2$-$G^3$, where $G^3$ denotes hydrogen,
D denotes O or $NR^{43}$, where $R^{43}$ denotes hydrogen or $C_1$–$C_3$-alkyl, and
$F^1$ denotes $C_2$–$C_4$-alkyl.

6. Compounds of the formula I according to claim 1, in which
$R^4$ denotes $G^1$-$F^2_{0,1}$-$G^2$-$G^3$, where $G^3$ denotes hydrogen, and
$F^2$ denotes $C_1$–$C_2$-alkyl.

7. Compounds of formula I according to claim 6, in which
$G^1$ denotes imidazole or pyrrole, where the pyrrole can in each case be substituted by at most three different or identical $R^5$ radicals, and
$F^2$ denotes $C_1$–$C_2$-alkyl.

8. Pharmaceutical composition which comprises at least one compound according to one of claim 1 and also at least one customary carrier and/or auxiliary substance.

9. Process for the treatment of a disease selected from the group consisting of damage due to ischaemias, microinfarctions, damage in association with a revascularization of critically stenosed coronary arteries or critically stenosed peripheral arteries, acute myocardial infarction and damage during and after its medicinal or mechanical lysis, leukemia, glioblastomers, lymphomas, melanomas, mammary and cervical carcinoma, sepsis, multiorgan failure, and diabetes mellitus by administering to a patient in need of such treatment of an effective quantity of at least one compound of the formula I according to claim 1.

10. Process for producing a compound according to claim 1, which comprises condensing an aldehyde of the formula II with a diamine of the formula III:

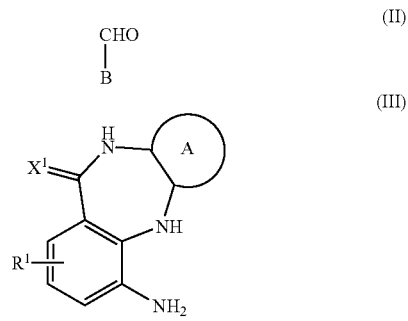

where the symbols in the formulae II and III have the same meaning as in claim 1.

11. Process according to claim 10, where the diamine of the formula III is obtained by reacting a substituted nitrobenzoic ester of the formula IV with a diamine of the formula V, in a polar solvent and in the presence of a base, and subsequently hydrogenating:

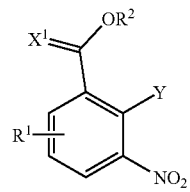
(IV)

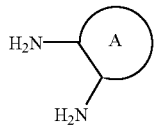
(V)

where $R^2$ denotes branched or unbranched, saturated or unsaturated $C_1$–$C_6$-alkyl and $Y^1$ is halogen.

* * * * *

UNITED STATES PATENT AND TRADEMARK OFFICE
CERTIFICATE OF CORRECTION

PATENT NO. : 7,026,311 B2
APPLICATION NO. : 10/041556
DATED : April 11, 2006
INVENTOR(S) : Wilfried Lubisch et al.

It is certified that error appears in the above-identified patent and that said Letters Patent is hereby corrected as shown below:

Column 13, line 5 reads "1Cyclohexylbenzo" and should be corrected to read "1-Cyclohexylbenzo".

Column 13, line 24 reads "1-(4Carboxyphenyl" and should be corrected to read "1-(4-Carboxyphenyl".

Column 16, line 36 reads "according to one of claim 1" and should be corrected to read "according to claim 1".

Signed and Sealed this

First Day of August, 2006

JON W. DUDAS
*Director of the United States Patent and Trademark Office*